United States Patent
Fotouhi et al.

(10) Patent No.: US 6,559,164 B1
(45) Date of Patent: May 6, 2003

(54) SUBSTITUTED PYRROLES SUITABLE FOR CONTINUOUS INFUSION

(75) Inventors: Nader Fotouhi, Chatham, NJ (US); Norman Kong, West Caldwell, NJ (US); Emily Aijun Liu, Nutley, NJ (US); Allen John Lovey, North Caldwell, NJ (US); John Guilfoyle Mullin, Jr., Hawthorne, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 245 days.

(21) Appl. No.: 09/678,521

(22) Filed: Oct. 3, 2000

Related U.S. Application Data
(60) Provisional application No. 60/158,860, filed on Oct. 12, 1999, and provisional application No. 60/185,648, filed on Feb. 29, 2000.

(51) Int. Cl.[7] ................... A61K 31/405; A61K 31/445; C07D 401/06; C07D 209/08
(52) U.S. Cl. .................. 514/315; 514/339; 514/414; 514/323; 546/251; 546/201; 548/415; 548/455
(58) Field of Search ................. 548/455, 415; 514/414, 339, 315, 323; 546/201, 251

(56) References Cited

U.S. PATENT DOCUMENTS
5,057,614 A   10/1991   Davis et al.
6,048,887 A   4/2000    Dhingra et al.

FOREIGN PATENT DOCUMENTS
WO  WO 91/13071   9/1991
WO  WO 98/04551   2/1998
WO  WO 99/47518   9/1999

OTHER PUBLICATIONS
J. Antibiotics vol. 48, No. 8, pp. 863–868 (1995).
J. Med. Chem. U.S. Am. Chem. Soc. vol. 35, No. 1 pp. 177–184 (1992).
Abstract corresponding to WO 91/13071 (Sep. 5, 1991).

*Primary Examiner*—Joseph K. McKane
*Assistant Examiner*—Ebenezer Sackey
(74) *Attorney, Agent, or Firm*—George W. Johnston; Patricia S. Rocha-Tramaloni

(57) ABSTRACT

Disclosed are novel substituted pyrroles having the formula

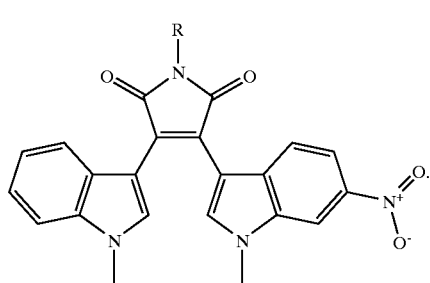

These compounds and their pharmaceutically acceptable salts are suitable for administration to patients as continuous infusion solution and are useful in the treatment and/or control of cell proliferative disorders, in particular cancer. Also disclosed are pharmaceutical compositions containing the foregoing compounds and methods for the treatment and/or control of cancer.

24 Claims, No Drawings

SUBSTITUTED PYRROLES SUITABLE FOR CONTINUOUS INFUSION

This application claims priority under 35 U.S.C. §119(e) of provisional application(s) Serial No. 60/158,860 filed on Oct. 12, 1999 and No. 60/185,648 filed on Feb. 29, 2000 respectively.

BRIEF SUMMARY OF THE INVENTION

The present invention is directed to certain substituted pyrroles that are antiproliferative agents. These compounds and their pharmaceutically acceptable salts are useful in the treatment or control of cell proliferative disorders, in particular cancer. The invention is also directed to pharmaceutical compositions containing such compounds, and to methods for the treatment and/or prevention of cancer, particularly the treatment or control of solid tumors.

BACKGROUND OF THE INVENTION

Uncontrolled cell proliferation is the hallmark of cancer. Cancerous tumor cells typically have some form of damage to the genes that directly or indirectly regulate the cell-division cycle. Much research has been expended in the study of antiproliferative agents. While many agents having desired antiproliferative activities have been identified, many of these agents have various drawbacks, including poor solubility, molecular complexity, etc., which may render them either unsuitable or inconvenient for therapeutic use in human patients. There continues to be a need for small molecule compounds that may be readily synthesized, are effective as cancer therapeutic agents and are suitable for continuous infusion delivery to patients. It is thus an object of this invention to provide such compounds as well as pharmaceutical compositions containing such compounds.

DEFINITIONS

As used herein, the following terms shall have the following definitions.

"Alkyl" denotes a straight-chain or branched saturated aliphatic hydrocarbon having 1 to 15, preferably 1 to 10, carbon atoms. Alkyl groups may be substituted as specifically provided infra. In addition the alkyl chain may include one or more hetero atoms in lieu of one or more carbon atoms. "Lower alkyl" groups having from 1 to 6, preferably 1 to 4, carbon atoms are preferred. Typical lower alkyl groups include methyl, ethyl, propyl, isopropyl, butyl, t-butyl, 2-butyl, pentyl, hexyl, and the like.

"Alkenyl" means a straight-chain or branched aliphatic unsaturated hydrocarbon having 1 to 15 carbon atoms, preferably 1 to 10 carbon atoms, most preferably 1 to 6 carbon atoms.

"Alkoxy" means an alkyl group that is attached to the remainder of the molecule by oxygen (e.g. RO—, such as methoxy, ethoxy, etc.).

"Aryl" means an aromatic ring having 5 to 10 atoms and consisting of 1 or 2 rings, which optionally may include one or more heteroatoms that are the same or different. For the purposes of this definition, aryl includes heteroaryl. Preferred heteroatoms include nitrogen, sulfur, or oxygen, singly or in any combination, in place of one or more of the carbons. Examples of aryl groups within this definition are phenyl, pyridine, imidazole, pyrrole, triazole, furan, pyrimidine.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective amount" means an amount of at least one compound of Formula I or a pharmaceutically acceptable salt thereof that significantly inhibits proliferation and/or prevents differentiation of a human tumor cell, including human tumor cell lines.

"Hetero atom" means an atom selected from nitrogen, sulfur and oxygen. Hetero atoms are independently selected and may replace one or more carbon atoms.

"Heterocycle" means a 3- to 10-membered non-aromatic, partially or completely saturated hydrocarbon group that contains at least one hetero atom. Such ring systems include, morpholine, pyrrolidine, piperidine, piperazine "$IC_{50}$" refers to the concentration of a particular compound according to the invention required to inhibit 50% of a specific measured activity. $IC_{50}$ can be. measured, inter alia, as is described in Example 26, infra.

"Pharmaceutically acceptable salt" refers to conventional acid-addition salts or base-addition salts which retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, phosphoric acid and nitric acid, and those derived from organic acids such as acetic acid, tartaric acid, salicylic acid, methanesulfonic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide.

"Pharmaceutically acceptable," such as pharmaceutically acceptable carrier, excipient, etc., means pharmacologically acceptable and substantially non-toxic to the subject to which the particular compound is administered.

"Pharmaceutically active metabolite" means a metabolic product of a compound of formula I which is pharmaceutically acceptable and effective.

"Plasma conversion" with respect to compounds of formula I means the degradation (enzymatic and/or non-enzymatic) of such compound in human or rodent plasma at 37° C. from 30 minutes to 6 hours to give 3-(1-methyl-3-indolyl)-4-(1-methyl-6-nitro-3-indolyl)-1H-pyrrole-2,5-dione, a pharmaceutically active metabolite of compounds of formula I, as well as pharmaceutically active metabolites thereof. This conversion is typically given as the percent degradation over a specified time frame.

"Polyethylene glycol" or "PEG" groups represent structures of the general formula $HO(CH_2CH_2O)_nR^8$, where n is on average between 2 and 1500, preferably 15 to 150, with an average molecular weight of 500 to 5000 Daltons, and wherein $R^8$ is carboxy or lower alkyl, preferably methyl or ethyl. PEG groups may be reacted with compounds according to this invention to yield pegylated compounds also within the scope of this invention.

"Prodrug" refers to a compound that may be converted under physiological conditions or by solvolysis to a pharmaceutical active compound. A prodrug may be inactive when administered to a subject but is converted in vivo to an active compound.

"Stability" is an overall assessment of the ability of a compound of formula I to withstand degradation in a typical solution used for the administration of drugs intravenously.

Specifically, it refers to the ability of any given compound of formula I to release 3-(1-methyl-3-indolyl)-4-(1-methyl-6-nitro-3-indolyl)-1H-pyrrole-2,5-dione, over a 72 hour period in a mixture of acetonitrile and saline or dextrose water. The "stability" of a compound of formula I is "very good" if the less than 1% 3-(1-Methyl-3-indolyl)-4-(1-methyl-6-nitro-3-indolyl)-1H-pyrrole-2,5-dione is detected, "good" if less than 2.5% 3-(1-Methyl-3-indolyl)-4-(1-methyl-6-nitro-3-indolyl)-1H-pyrrole-2,5-dione is detected, and "fair" if less than 5% 3-(1-Methyl-3-indolyl)-4-(1-methyl-6-nitro-3-indolyl)-1H-pyrrole-2,5-dione is detected after 72 hours incubation at room temperature.

"Substituted," as in substituted alkyl, means that the substitution can occur at one or more positions and, unless otherwise indicated, that the substituents at each substitution site are independently selected from the specified options.

"Substituted amino" means an amino group which is mono- or di-substituted with another group, preferably lower alkyl (e.g. methyl, or ethyl).

DETAILED DESCRIPTION OF THE INVENTION

Specifically, the invention relates to substituted pyrroles having the formula:

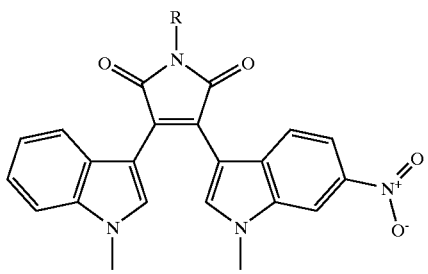

I and pharmaceutically acceptable salts of the foregoing compounds, wherein

R is selected from the group consisting of —CH$_2$OPO$_3$R$^1$R$^2$, —CH$_2$OH, —CH$_2$OCOR$^3$, —CH$_2$OCO$_2$R$^3$, —CH$_2$OCONHR$^3$, and —CONHR$^3$;

R$^1$ and R$^2$ are selected from the group consisting of H, Na and NH$_4$ and are the same unless either R$^1$ or R$^2$ is H, in which case the other can be different, or alternatively, R$^1$ and R$^2$ together represent calcium.

R$^3$ is selected from the group consisting of alkyl which optionally may be substituted by one or more substituents selected from the group consisting of —CO$_2$R$^4$, —NR$^5$R$^6$, polyethylene glycol, —OPO$_3$R$^1$R$^2$, hydroxy, alkoxy and aryl; alkenyl which optionally may be substituted by one or more substituents selected from the group consisting of —CO$_2$R$^4$, —NR$^5$R$^6$, polyethylene glycol, —OPO$_3$R$^1$R$^2$, hydroxy, alkoxy and aryl; cycloalkyl which optionally may be substituted by one or more substituents selected from the group consisting of —CO$_2$R$^4$, —NR$^5$R$^6$, polyethylene glycol, —OPO$_3$R$^1$R$^2$, hydroxy, alkoxy and aryl;

heterocycle, which when including N as a heteroatom, the N optionally may be substituted with lower alkyl and —COR$^7$, aryl which optionally may be substituted by one or more substituents selected from the group consisting of CO$_2$R$^4$, hydroxy, alkoxy, polyethylene glycol, OPO$_3$R$^1$R$^2$, and alkyl which itself may be substituted with hydroxy alkoxy, carboxy and substituted amino, provided that when aryl represents pyridine, the nitrogen may be substituted with lower alkyl;

R$^4$ is selected from the group consisting of H, Na and lower alkyl;

R$^5$ and R$^6$ are each independently selected from the group consisting of H, lower alkyl, and —COR$^7$, or alternatively, the group —NR$^5$R$^6$ together form a 5 or 6 membered heterocyclic ring; and R$^7$ is lower alkyl which optionally may be substituted with carboxy, polyethylene glycol and substituted amino.

The compounds of formula I have antiproliferative activity, specifically, they inhibit cell division in G2/M phase of the cell cycle and are generally referred to as "G2/M phase cell-cycle" inhibitors. These compounds are stable, soluble prodrugs of an anticancer therapeutic agent within U.S. Pat. No. 5,057,614 and are thus suitable for continuous infusion delivery.

The present invention is further directed to pharmaceutical compositions comprising a pharmaceutically effective amount of any one or more of the above-described compounds and a pharmaceutically acceptable carrier or excipient.

The present invention is also directed to a method for treating solid tumors, in particular breast or colon tumors, by administering to a human patient in need of such therapy an effective amount of a compound of formula I and/or its pharmaceutically acceptable salts.

In a preferred embodiment of the compounds of formula I, R is selected from the group consisting of —CH$_2$OPO$_3$R$^1$R$^2$, —CH$_2$OCOR$^3$, —CH$_2$OCO$_2$R$^3$, —CH$_2$OCONHR$^3$, and —CONHR$^3$, preferably —CH$_2$OPO$_3$R$^1$R$^2$, —CH$_2$OCOR$^3$ and —CONHR$^3$, most preferably —CH$_2$OPO$_3$R$^1$R$^2$ and —CH$_2$OCOR$^3$.

In another preferred embodiment of the compounds of formula I, R is —CH$_2$OCO-pyridine wherein the N atom on the pyridine is substituted with lower alkyl, most preferably methyl or ethyl, thereby creating a quaternary nitrogen atom.

In another preferred embodiment of the compounds of formula I, R$^1$ and R$^2$ are independently selected from the group consisting of H and Na.

In another preferred embodiment of the compounds of formula I, R$^3$ is heterocycle containing at least one nitrogen atom that optionally may be substituted with —COR$^7$.

In another preferred embodiment of the compounds of formula I, R$^3$ is aryl which is substituted with —OPO$_3$R$^1$R$^2$, and R$^1$ and R$^2$ are independently selected from H or Na.

In another preferred embodiment of the compounds of formula I, R$^3$ is aryl which is substituted by the group consisting of —CO$_2$Na, polyethylene glycol and —CH$_2$CH$_2$N(CH$_2$CH$_2$)$_2$.

In another preferred embodiment of the compounds of formula I, R$^3$ is lower alkyl which is substituted with —CO$_2$Na.

In another preferred embodiment of the compounds of formula I, the group NR$^5$R$^6$ together forms a 5 or 6 membered heterocyclic ring, preferably piperidine or pyrrolidine.

In another preferred embodiment of the compounds of formula I, R$^5$ and R$^6$ are each independently selected from the group consisting of H, methyl and ethyl.

In another preferred embodiment of the compounds of formula I, R$^7$ is ethyl which is substituted with polyethylene glycol.

In another preferred embodiment of the compounds of formula I, the polyethylene glycol has a molecular weight of from about 750 to about 5000 Daltons.

In another preferred embodiment of the compounds of formula I, R is —CH$_2$OCOR$^3$, wherein R$^3$ is ethyl which is substituted with PEG having a molecular weight of from about 750 to about 5000 Daltons.

The following are examples of preferred compounds of formula I:

phosphoric acid mono-[3-(1-methyl-1H-indol-3-yl)-4-(1-methyl-6-nitro-1H-indol-3-yl)-2,5-dioxo-2,5-dihydro-pyrrol-1-ylmethyl]sodium salt, O-[2-[[2,5-dihydro-3-(1-methyl-1H-indol-3-yl)-4-(1-methyl-6-nitro-1H-indol-3-yl)-2,5-dioxo-2,5-dihydro-pyrrol-1-yl]methoxycarbonyl]ethyl]-O'-methylpolyethylene glycol 2000, phosphoric acid mono-(4-{[3-(1-methyl-1H-indol-3-yl)-4-(1-methyl-6-nitro-1H-indol-3-yl)-2,5-dioxo-2,5-dihydro-pyrrole-1-carbonyl]-amino}butyl) ester sodium salt, 1-methyl-3-[3-(1-methyl-1H-indol-3-yl)-4-(1-methyl-6-nitro-1H-indol-3-yl)-2,5-dioxo-2,5-dihydro-pyrrol-1-ylmethoxycarbonyl]-pyridinium trifluoroacetate, 1-hydroxymethyl-3-(1-methyl-1H-indol-3-yl)-4-(1-methyl-6-nitro-1H-indol-3-yl)-pyrrole-2,5-dione; and O-[2-[[[2,5-Dihydro-3-(1-methyl-1H-indol-3-yl)-4-(1-methyl-6-nitro-1H-indol-3-yl)-2,5-dioxo-1H-pyrrol-1-yl]methoxy]carbonyl]methyl]-O'-methylpolyethylene glycol 2000.

The compounds disclosed herein and covered by the above formulae may exhibit tautomerism or structural isomerism. It is intended that the invention encompasses any tautomeric or structural isomeric form of these compounds, or mixtures of such forms, and is not limited to any one tautomeric or structural isomeric form utilized within the formulae drawn above.

SYNTHESIS OF COMPOUNDS ACCORDING TO THE INVENTION

The compounds of the invention may be prepared by processes known in the art. Suitable processes for synthesizing these compounds are provided in the examples. Generally, these compounds may be prepared according to the following synthesis schemes.

Compounds of formula I, in which R signifies CH$_2$OCOR$^3$, and in which R$^3$ is as described above, may be prepared as indicated in scheme I below, provided that if R$^3$ contains a hydroxy, hydroxyalkyl, amino, aminoalkyl, monoalkylamino, or carboxyl, such group is first protected with a conventional protective group know to those skilled in the art. Scheme I is also useful to prepare compounds of formula I wherein R is —CH$_2$OH.

Scheme I

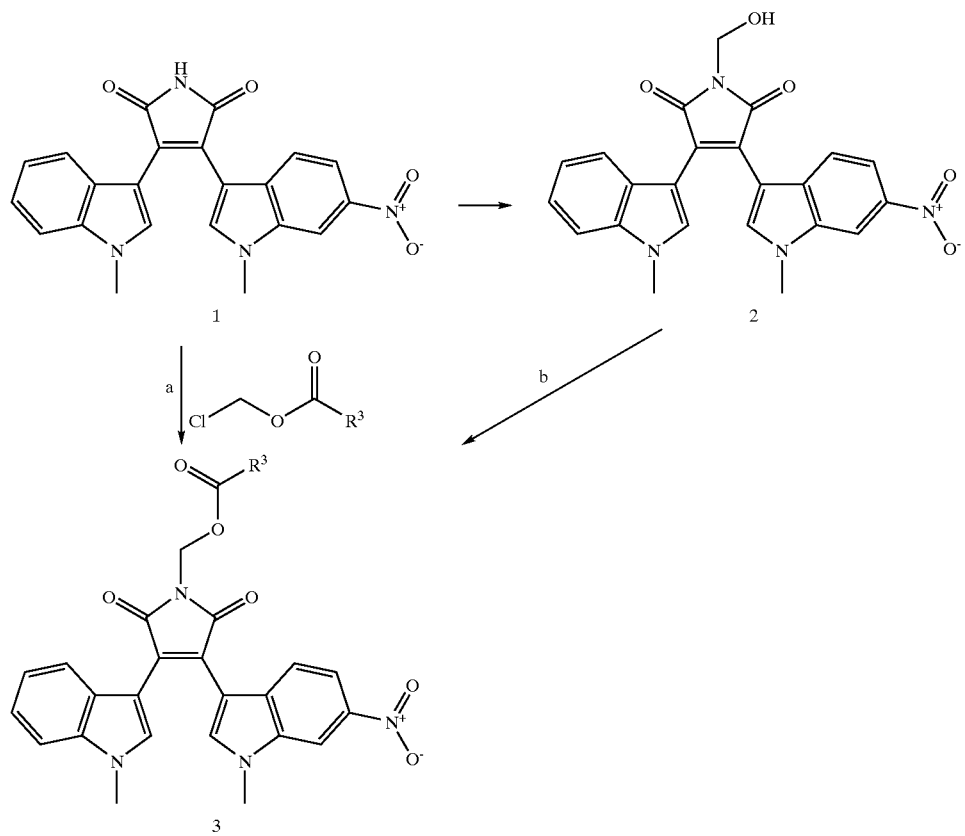

As indicated in scheme Ia, a chloromethyl ester prepared by reacting a known carboxylic acid or a carboxylic acid prepared by known methods, with $ClCH_2OSO_2Cl$ in methylene chloride and water, in the presence of a base such as sodium carbonate and a phase transfer catalyst such as tetrabutylammoniumhydrogen sulfate, was reacted with 3-(1-methyl-3-indolyl)-4-(1-methyl-6-nitro-3-indolyl)-1H-pyrrole-2,5-dione [prepared as exemplified in Davis U.S. Pat. No. 5,057,614].

Alternatively, 3-(1-methyl-3-indolyl)-4-(1-methyl-6-nitro-3-indolyl)-1H-pyrrole-2,5-dione [prepared as exemplified in Davis U.S. Pat. No. 5,057,614] is treated with formaldehyde to yield the hydroxymethyl intermediate 2. This intermediate is then esterified using known procedures. Typically, the hydroxy intermediate 2 is treated with a known carboxylic acid or a carboxylic acid prepared by known methods, in a solvent such as methylene chloride in the presence of EDC and dimethylaminopyridine for several hours at room temperature. Alternatively, the hydroxy intermediate 2 may be treated with a known acid chloride or an acid chloride prepared from known methods.

To prepare compounds of structure 3 wherein $R^3$ contains a heteroaromatic ring, the heteroatom such as N may be further modified by reaction with an alkyl iodide such as $CH_3I$ in a solvent such as acetonitrile. Alternatively compounds of structure 3 wherein $R^3$ contains a suitably protected hydroxy, hydroxyalkyl, amino, aminoalkyl, monoalkylamino, may be further modified by first removing the protective group by known methods. The amino or hydroxy group can then be modified to the desired amide or ester by methods known in the art.

Compounds of the general formula I in which R signifies $-CH_2OPO_3R^1R^2$, and wherein $R^1$ and $R^2$ are as defined above, can be prepared by the following scheme (II).

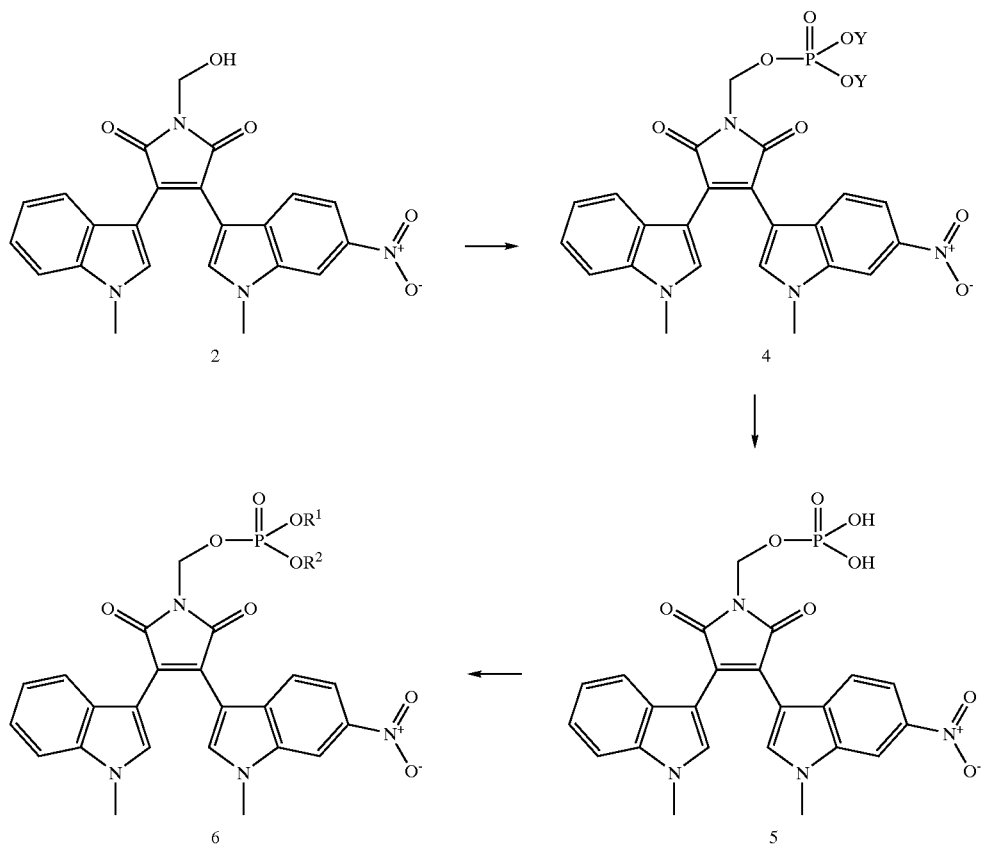

Scheme II

Typically, hydroxymethyl intermediate 2 is coupled with a suitably protected phosphate by a mitsunobu reaction using triphenylphosphine and diethylazodicarboxylate to give compound of structure 4 in which Y represents a suitable protecting group. Removal of the protecting groups may be achieved by any of the standard methods to give the phosphoric acid 5. In particular, when Y represents a benzyl group, the protective groups are removed by using cyclohexadiene and palladium on carbon as a catalyst. Compound 5 can then be converted to its salt, such as a monosodium salt 6, by standard methods.

Compounds of formula I, in which R signifies —$CH_2OCO_2R^3$, and in which $R^3$ is as described above, were prepared according to scheme III below.

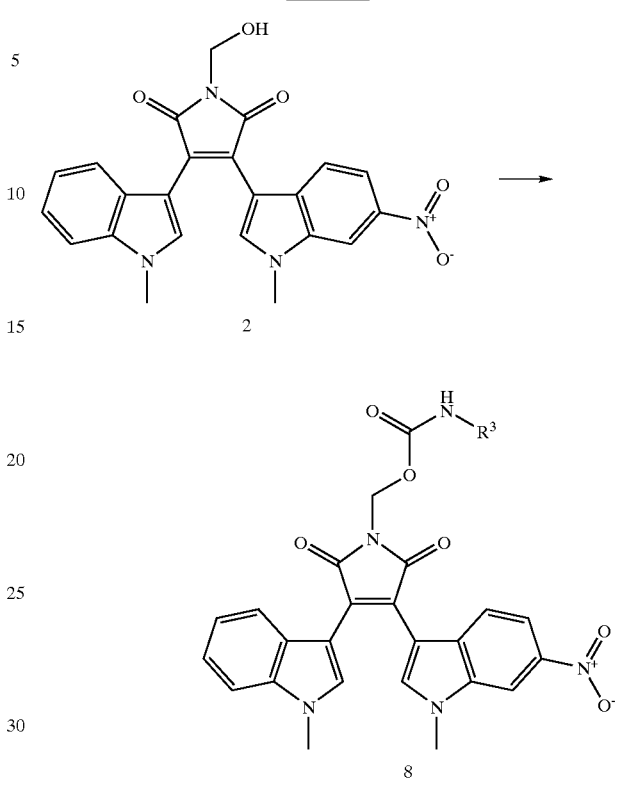

Typically, hydroxymethyl intermediate 2 is treated with a known chloroformate or a chloroformate prepared using known procedures, in a solvent such as THF at temperatures of 50 to 20° C., in the presence of dimethylaminopyridine and 1,5-diazabicyclo(4.3.0)non-5-ene to afford the desired carbonate.

Compounds of formula I, in which R signifies —$CH_2OCONHR^3$, and in which $R^3$ is as described above, were prepared as described in scheme IV below.

Scheme IV

[Structure 2]

[Structure 8]

Typically, hydroxymethyl intermediate 2 is deprotonated using a strong base such as n-butyllithiuim or lithium bis(trimethylsilyl)amide in a solvent such as THF at 0° C. The anion generated is then treated in the same solvent with bis(p-nitrophenyl)carbonate, followed by a known amine or an amine prepared using known procedures.

Compounds of formula I, in which R signifies —$CONHR^3$, and in which $R^3$ is as defined above, may be prepared as indicated in scheme V, provided that if $R^3$ contains a hydroxy, hydroxyalkyl, amino, aminoalkyl, monoalkylamino, or carboxyl, such group is protected with a conventional protective group.

Scheme V

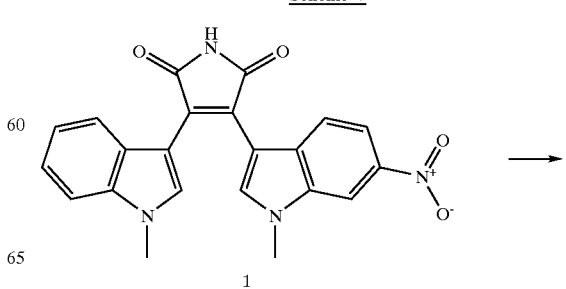

-continued

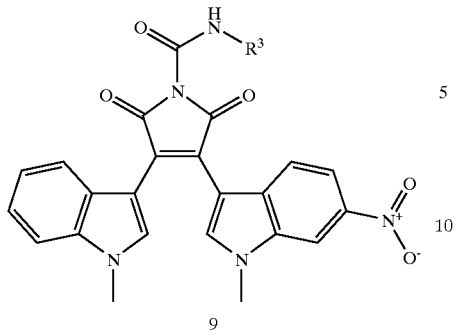

9

Typically, 3-(1-Methyl-3-indolyl)-4-(1-methyl-6-nitro-3-indolyl)-1H-pyrrole-2,5-dione [prepared as exemplified in Davis U.S. Pat. No. 5,057,614] is deprotonated in an aprotic solvent such as THF at 0° C. using a strong base such as n-butyllithiuim or lithium bis(trimethylsilyl)amide. The resulting anion is then treated with bis(p-nitrophenyl) carbonate, followed by a known amine or an amine prepared by methods known in the art.

The conversion of an acidic compound of formula I into a pharmaceutically acceptable salt can be carried out by treatment with a suitable base in a known manner. Suitable salts are those derived not only from inorganic bases, for example, sodium, potassium or calcium salts, but also from organic bases such as ethylenediamine, monoethanolamine or diethanolamine. The conversion of a basic compound of formula I into a pharmaceutically acceptable salt can be carried out by treatment with a suitable acid in a known manner. Suitable salts are those described on page 3.

COMPOSITIONS/FORMULATIONS

In an alternative embodiment, the present invention is directed to pharmaceutical compositions comprising at least one compound of formula I or a pharmaceutically acceptable salt thereof.

These pharmaceutical compositions can be administered orally, for example, in the form of tablets, coated tablets, dragees, hard or soft gelatin capsules, solutions, emulsions or suspensions. They can also be administered rectally, for example, in the form of suppositories. In particular, however, the compounds of the present invention are suitable for parenteral administration, for example, in the form of injection solutions.

The pharmaceutical compositions of the present invention comprising compounds of formula I, prodrugs of such compounds, or the salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

DOSAGES

As mentioned above, the compounds of the present invention are useful in the treatment or control of cell proliferative disorders, in particular oncological disorders. These compounds and formulations containing said compounds are particularly useful in the treatment or control of solid tumors, such as, for example, breast and colon tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and will be adjusted to the individual requirements in each particular case. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

EXAMPLES

The compounds of the present invention may be synthesized according to known techniques, such as, for example, the general schemes provided above. The following examples illustrate preferred methods for synthesizing the compounds and formulations of the present invention.

Example 1

Phosphoric Acid Mono-[3-(1-methyl-1H-indol-3-yl)-4-(1-methyl-6-nitro-1H-indol-3-yl)-2,5-dioxo-2,5-dihydro-pyrrol-1-ylmethyl]sodium Salt a) A suspension consisting of 0.5 g (1.25 mmole) of 3-(1-methyl-3-indolyl)-4-(1-methyl-6-nitro-3-indolyl)-1H-pyrrole-2,5-dione (See Davis U.S. Pat. No. 5,057,614), 4.0 ml of formaldehyde solution (37% w/w), and 2.0 ml of water was heated to 125° C. with stirring and with a reflux condensed attached for 14 hours. The reaction mixture was cooled and diluted with water. The red solid was filtered, washed with water and dried. The solid was purified by chromatography using silica gel and a mixture of EtOAc/Hexane as elutant to afford 1-hydroxymethyl-3-(1-methyl-1H-indol-3-yl)-4-(1-methyl-6-nitro-1H-indol-3-yl)-pyrrole-2,5-dione (mp=209–211° C.).

b) To a cool solution (10° C.) of THF containing 0.12 g (0.68 mmole) of diethylazodicarboxylate, 0.20 g (0.46 mmole) of 1-hydroxymethyl-3-(1-methyl-1H-indol-3-yl)-4-(1-methyl-6-nitro-1H-indol-3-yl)-pyrrole-2,5-dione (from Step a above), and 0.40 g (1.43 mmole) of dibenzylphosphate was added dropwise 5 ml of a solution containing 0.128 g (0.49 mmole) of triphenylphosphine. The resulting mixture was stirred for 14 hours at 20° C. All solvent was evaporated and the residue was purified by chromatography using silica gel and eluting with a mixture of EtOAc/Hexanes to afford phosphoric acid dibenzyl ester 3-(1-methyl-1H-indol-3-yl)-4-(1-methyl-6-nitro-1H-indol-3-yl)-2,5-dioxo-2,5-dihydro-pyrrol-1-ylmethyl ester as a brick red solid (mp=105–109° C.).

c) A solution of 35 mg (0.051 mmole) of phosphoric acid dibenzyl ester 3-(1-methyl-1H-indol-3-yl)-4-(1-methyl-6-nitro-1H-indol-3-yl)-2,5-dioxo-2,5-dihydro-pyrrol-1-ylmethyl ester (from step b above) in THF (5 ml) with 5 ml ethanol and 0.5 g of 1,4-cyclohexadiene was treated with 35 mg of 10% Palladium/carbon. The mixture was heated to 45° C. at which point there was a slight exotherm. After 10 min. at 50° C., the reaction was filtered hot through celite and the filter cake was washed with THF. All solvent was evaporated and the residue was redissolved in THF, filtered through celite and triturated with hexane to give 14 mg of phosphoric acid mono-[3-(1-methyl-1H-indol-3-yl)-4-(1-methyl-6-nitro-1H-indol-3-yl)-2,5-dioxo-2,5-dihydro-pyrrol-1-ylmethyl].

d) A solution of 14 mg (0.029 mmole) of phosphoric acid mono-[3-(1-methyl-1H-indol-3-yl)-4-(1-methyl-6-nitro-1H-indol-3-yl)-2,5-dioxo-2,5-dihydro-pyrrol-1-ylmethyl] (from step c above) in 15 ml of water was treated with dilute sodium hydroxide until the pH of the solution was 7.1. This solution was filtered and lyophilized to afford phosphoric acid mono-[3-(1-methyl-1H-indol-3-yl)-4-(1-methyl-6-nitro-1H-indol-3-yl)-2,5-dioxo-2,5-dihydro-pyrrol-1-ylmethyl]sodium salt.

Example 2

Isonicotinic Acid 3-(1-Methyl-1H-indol-3-yl)-4-(1-methyl-6-nitro-1H-indol-3-yl)-2,5-dioxo-2,5-dihydro-pyrrol-1-ylmethyl Ester To a solution of dimethylaminopyridine (1.5 equivalents) and 1-ethyl-3-(3-dimethylaminopropyl)carbodiimide hydrochloride (1.5 equivalent) in $CH_2Cl_2$ was added 4-picolinic acid (1.2 equivalents) and the reaction mixture was stirred a few minutes. 1-Hydroxymethyl-3-(1-methyl-1H-indol-3-yl)-4-(1-methyl-6-nitro-1H-indol-3-yl)-pyrrole-2,5-dione, prepared as in example 1a, was added and the reaction mixture was stirred at room temperature for several hours. The mixture was diluted with dichloromethane, washed with aqueous HCL, saturated $NaHCO_3$, water, dried over $MgSO_4$ and evaporated. The residue was purified by column chromatography to afford isonicotinic acid 3-(1-methyl-1H-indol-3-yl)-4-(1-methyl-6-nitro-1H-indol-3-yl)-2,5-dioxo-2,5-dihydro-pyrrol-1-ylmethyl ester (yield—76%).

Example 3

Using the same procedure as in example 2 the following compounds were prepared:

a) nicotinic acid 3-(1-methyl-1H-indol-3-yl)-4-(1-methyl-6-nitro-1H-indol-3-yl)-2,5-dioxo-2,5-dihydro-pyrrol-1-ylmethyl ester (yield—76%);
b) O-[2-[[2,5-dihydro-3-(1-methyl-1H-indol-3-yl)-4-(1-methyl-6-nitro-1H-indol-3-yl)-2,5-dioxo-2,5-dihydro-pyrrol-1-yl]methoxycarbonyl]ethyl]-O'-methylpolyethylene glycol 2000 (yield—88%);
c) pyridin-4-yl acetic acid 3-(1-methyl-1H-indol-3-yl)-4-(1-methyl-6-nitro-1H-indol-3-yl)-2,5-dioxo-2,5-dihydro-pyrrol-1-ylmethyl ester (yield—39%);
d) pyridin-3-yl acetic acid 3-(1-methyl-1H-indol-3-yl)-4-(1-methyl-6-nitro-1H-indol-3-yl)-2,5-dioxo-2,5-dihydro-pyrrol-1-ylmethyl ester (yield—94%);
e) pyridin-2-yl acetic acid 3-(1-methyl-1H-indol-3-yl)-4-(1-methyl-6-nitro-1H-indol-3-yl)-2,5-dioxo-2,5-dihydro-pyrrol-1-ylmethyl ester (yield—65%);
f) succinic acid mono-[3-(1-methyl-1H-indol-3-yl)-4-(1-methyl-6-nitro-1H-indol-3-yl)-2,5-dioxo-2,5-dihydro-pyrrol-1-ylmethyl] ester (used 3eq EDC and DMAP and 2.4 eq acid, purified by preparative TLC) (yield—89%);
g) hexadec-9-enoic 3-(1-methyl-1H-indol-3-yl)-4-(1-methyl-6-nitro-1H-indol-3-yl)-2,5-dioxo-2,5-dihydro-pyrrol-1-ylmethyl ester (yield—53%);
h) [2-[2-(2-carboxymethoxy-ethoxy)-ethoxy]-ethoxy] acetic acid-3-(1-methyl-1H-indol-3-yl)-4-(1-methyl-6-nitro-1H-indol-3-yl)-2,5-dioxo-2,5-dihydro-pyrrol-1-ylmethyl ester, purified by reverse phase column chromatography (yield—61%).

Example 4

But-2-enedioic Acid Mono-[3-(1-methyl-1H-indol-3-yl)-4-(1-methyl-6-nitro-1H-indol-3-yl)-2,5-dioxo-2,5-dihydro-pyrrol-1-ylmethyl] Ester To a solution of 1-Hydroxymethyl-3-(1-methyl-1H-indol-3-yl)-4-(1-methyl-6-nitro-1H-indol-3-yl)-pyrrole-2,5-dione, prepared as in example 1a, in 1:4 $CH_2Cl_2$:benzene, were added a large excess of fumaryl chloride and excess diisopropylethylamine. The reaction was stirred at room temperature for 20 min. Acetone and water were, added. The reaction mixture was diluted with $CH_2Cl_2$, washed with water, cold saturated $NaHCO_3$, water and dried over $Na_2SO_4$. The resulting but-2-enedioic acid mono-[3-(1-methyl-1H-indol-3-yl)-4-(1-methyl-6-nitro-1H-indol-3-yl)-2,5-dioxo-2,5-dihydro-pyrrol-1-ylmethyl] ester was purified by flash chromatography (yield 60%).

Example 5

Decanoic Acid 3-(1-Methyl-1H-indol-3-yl)-4-(1-methyl-6-nitro-1H-indol-3-yl)-2,5-dioxo-2,5-dihydro-pyrrol-1-ylmethyl Ester a) Decanoic acid (0.2 gm, 1.2 mmol) was treated with 4 eq $NaHCO_3$, 0.1 eq $Bu_4NHSO_4$ and, 1.2 eq $ClCH_2OSO_2Cl$ in 1:1 $CH_2Cl_2$:$H_2O$. The reaction was stirred vigorously at 0° C. for 30 min then room temperature ("RT") for 3 hrs. Aqueous workup yielded chloromethyldecanoate (yield 100%).

b) 3-(1-Methyl-3-indolyl)-4-(1-methyl-6-nitro-3-indolyl)-1H-pyrrole-2,5-dione (20 mg 0.05 mmol) (See Davis U.S. Pat. No. 5,057,614) was dissolved in DMF and treated with $Cs_2CO_3$ (49 mg, 0.15 mmol) for a few minutes, the chloromethyl ester (33 mg, 0.15 mmol) prepared in step a) above was added and the reaction was stirred at room temperature for 30 minutes. Aqueous workup, followed by purification by flash chromatography yielded decanoic acid 3-(1-methyl-1H-indol-3-yl)-4-(1-methyl-6-nitro-1H-indol-3-yl)-2,5-dioxo-2,5-dihydro-pyrrol-1-ylmethyl ester (yield—58%).

Example 6

The following compounds were prepared in a similar manner to example 5b above:

a) [2-(2-methoxy-ethoxy)-ethoxy]-acetic acid 3-(1-methyl-1H-indol-3-yl)-4-(1-methyl-6-nitro-1H-indol-3-yl)-2,5-dioxo-2,5-dihydro-pyrrol-1-ylmethyl ester (the starting chloromethyl ester was prepared from the corresponding acid as described in example 5a; purified by preparative TLC) (yield—38%);

b) 2,2-dimethyl propionic acid 3-(1-methyl-1H-indol-3-yl)-4-(1-methyl-6-nitro-1H-indol-3-yl)-2,5-dioxo-2,5-dihydro-pyrrol-1-ylmethyl ester (the starting chloromethyl pivalate was purchased from (Aldrich) (yield—91%).

Example 7

3-Amino-cyclohexanecarboxylic Acid 3-(1-Methyl-1H-indol-3-yl)-4-(1-methyl-6-nitro-1H-indol-3-yl)-2,5-dioxo-2,5-dihydro-pyrrol-1-ylmethyl Ester Trifluoroacetate a) chloromethyl-N-t-butyloxycarbonyl-3-amino-cyclohexanecarboxylate was prepared in a similar manner (87% yield) as described in example 5a from N-t-butyloxycarbonyl-3-amino-cyclohexanecarboxylic acid which itself was synthesized by the known procedure of BOC protection of 3-amino-cyclohexanecarboxylic acid (Aldrich).

b) 3-(1-Methyl-3-indolyl)-4-(1-methyl-6-nitro-3-indolyl)-1H-pyrrole-2,5-dione (68 mg, 0.15 mmol) (see Davis U.S. Pat. No. 5,057,614) was dissolved in DMF and treated with $Cs_2CO_3$ (0.15 g, 0.45 mmol) for a few minutes. The chloromethyl ester (0.13 gm, 0.45 mmol) prepared in step a) above was added and the reaction mixture was stirred at room temperature for 50 minutes. Aqueous workup, followed by purification by flash chromatography yielded [N-a-butlyloxy-3-amino-cyclohexanecarboxylic acid]-3-(1-methyl-1H-indol-3-yl)-4-(1-methyl-6-nitro-1H-indol-3-yl)-2,5-dioxo-2,5-dihydro-pyrrol-1-ylmethyl ester (yield—95%)

c) The tert-butyloxy protecting group of the compound of step b) above was removed by treatment with TFA in $CH_2Cl_2$ at room temperature for 50 minutes. The TFA and $CH_2Cl_2$ were evaporate using a stream of nitrogen. The residue was purified by HPLC to give 3-amino-cyclohexanecarboxylic acid 3-(1-methyl-1H-indol-3-yl)-4-(1-methyl-6-nitro-1H-indol-3-yl)-2,5-dioxo-2,5-dihydro-pyrrol-1-ylmethyl ester trifluoroacetate (yield—57%).

Example 8

The following compounds were prepared in a similar manner to example 7a,b and c described above:
a) piperidine-4-carboxylic acid 3-(1-methyl-1H-indol-3-yl)-4-(1-methyl-6-nitro-1H-indol-3-yl)-2,5-dioxo-2,5-dihydro-pyrrol-1-ylmethyl ester trifluoroacetate (prepared from N-t-butyloxycarbonyl-piperidine-4-carboxylic acid (Bachem)) (yield—62%);
b) 2-amino-2-methyl-propionic acid 3-(1-methyl-1H-indol-3-yl)-4-(1-methyl-6-nitro-1H-indol-3-yl)-2,5-dioxo-2,5-dihydro-pyrrol-1-ylmethyl ester trifluoroacetate (prepared from N-t-butyloxycarbonyl-aminoisobutyric acid (Bachem)) (yield—63%).

Example 9

Piperidine-4-carboxylic acid 3-(1-Methyl-1H-indol-3-yl)-4-(1-methyl-6-nitro-1H-indol-3-yl)-2,5-dioxo-2,5-dihydro-pyrrol-1-ylmethyl Ester Acetate Salt Piperidine-4-carboxylic acid 3-(1-methyl-1H-indol-3-yl)-4-(1-methyl-6-nitro-1H-indol-3-yl)-2,5-dioxo-2,5-dihydro-pyrrol-1-ylmethyl ester trifluoroacetate, prepared as in example 8a above, was dissolved in ethyl acetate. The resulting solution was neutralized with cold saturated $NaHCO_3$. The ethyl acetate layer was concentrated and slurried in $H_2O$ and acidified with excess HOAc and lyophilized to give the desired product (yield—97%).

Example 10

Piperidine-4-carboxylic Acid 3-(1-Methyl-1H-indol-3-yl)-4-(1-methyl-6-nitro-1H-indol-3-yl)-2,5-dioxo-2,5-dihydro-pyrrol-1-ylmethyl Ester Hydrochloride Piperidine-4-carboxylic acid 3-(1-methyl-1H-indol-3-yl)-4-(1-methyl-6-nitro-1H-indol-3-yl)-2,5-dioxo-2,5-dihydro-pyrrol-1-ylmethyl ester acetate salt, prepared as in example 9 above, was dissolved in ethyl acetate. The ethyl acetate solution was neutralized with cold saturated $NaHCO_3$, was concentrated, and was taken up in 1:5 $CH_3CN:H_2O$. The resulting solution was treated with 2 equivalents of 2N aq. HCl and purified by HPLC to give the desired product (yield—86%).

Example 11

2-Amino-2-methyl-propionic Acid 3-(1-Methyl-1H-indol-3-yl)-4-(1-methyl-6-nitro-1H-indol-3-yl)-2,5-dioxo-2,5-dihydro-pyrrol-1-ylmethyl Ester Hydrochloride This compound was prepared from 2-amino-2-methyl-propionic acid 3-(1-methyl-1H-indol-3-yl)-4-(1-methyl-6-nitro-1H-indol-3-yl)-2,5-dioxo-2,5-dihydro-pyrrol-1-ylmethyl ester trifluoroacetate, prepared as in example 8b, using a similar procedure as described in example 10 (yield—71%).

Example 12

1-Methyl-3-[3-(1-methyl-1H-indol-3-yl)-4-(1-methyl-6-nitro-1H-indol-3-yl)-2,5-dioxo-2,5-dihydro-pyrrol-1-ylmethoxycarbonyl]-pyridinium; Trifluoroacetate A solution of nicotinic acid 3-(1-methyl-1H-indol-3-yl)-4-(1-methyl-6-nitro-1H-indol-3-yl)-2,5-dioxo-2,5-dihydro-pyrrol-1-ylmethyl ester in $CH_3CN$, prepared as described in example 3a, was treated with 2 eq $NaBPh_4$ and 6 eq MeI. The reaction was stirred at reflux for 7 hours. The solvent was evaporated and the residue was purified by HPLC to afford 1-methyl-3-[3-(1-methyl-1H-indol-3-yl)-4-(1-methyl-6-nitro-1H-indol-3-yl)-2,5-dioxo-2,5-dihydro-pyrrol-1-ylmethoxycarbonyl]-pyridinium; trifluoroacetate (yield 52%).

Example 13

O-[2-[[4-[[[2,5-Dihydro-3-(1-Methyl-1H-indol-3-yl)-4-(1-methyl-6-nitro-1H-indol-3-yl)-2,5-dioxo-1H-pyrrol-1-yl]methoxy]carbonyl]-1-piperidinyl] carbonyl]ethyl]-O'-methylpolyethylene Glycol 1000

3-(1-Methyl-3-indolyl)-4-(1-methyl-6-nitro-3-indolyl)-1-(4-piperidinecarboxymethyl)-1H-pyrrole-2,5-dione trifluoroacetate, prepared as in example 8a, was dissolved in ethyl acetate. The resulting solution was neutralized with cold saturated $NaHCO_3$. The ethyl acetate layer was concentrated and the residue was taken up in $CH_3CN$. The solution was added dropwise to a solution of O-(2-carboxyethyl)-O'-methylpolyethylene glycol 1000 acid chloride (prepared from O-(2-carboxyethyl)-O'-methylpolyethylene glycol 1000 acid using standard procedure) in $CH_3CN$. The reaction mixture was stirred for 1 hour. The solvent was evaporated and the residue was purified by HPLC (yield 70%).

Example 14

4-Phosphonooxy-benzoic Acid 3-(1-Methyl-1H-indol-3-yl)-4-(1-methyl-6-nitro-1H-indol-3-yl)-2,5-dioxo-2,5-dihydro-pyrrol-1-ylmethyl Ester Monosodium Salt a) t-BuOK (9.6 mL, 9.6 mmol, 1M in THF) was added drop-wise to a solution of 4-hydroxybenzaldehyde (1.10 g, 9 mmol) in THF (40 mL). The mixture was heated at 70° C. and tetrabenzyl pyrophosphate (5.05 g, 9.37 mmol) in THF (20 mL) was added. After 1 h, THF (100 mL) and hexanes (200 mL) were added. The reaction mixture was filtered and the filtrate was evaporated. Chromatography of the residue over silica using 2%–5%–10% methanol-$CH_2Cl_2$ gave phosphoric acid dibenzyl ester 4-formyl-phenyl ester (3.38 g, 98%).

b) Sodium dihyrogenphosphate monohydrate (79 mg, 0.57 mmol) in water (1 mL) was added to a solution of phosphoric acid dibenzyl ester 4-formyl-phenyl ester (0.89 g, 2.32 mml) (from step a) above) in MeCN (10 mL) at 0° C. Hydrogen peroxide (0.24 mL, 30% in water, 2.4 mmol) was added, followed by sodium chlorite (315 mg, 3.5 mmol) in water (2 mL). The reaction mixture was stirred at 0° C. for 1 h, then warmed to room temperature for 2 h. Sodium thiosulfate (100 mg) was added and the reaction mixture was vigorously stirred for 15 min. Water was added and the mixture was extracted with EtOAc. The organic extracts were washed with water, dried ($MgSO_4$), filtered and concentrated to give phosphoric acid dibenzyl ester 4-carboxyl-phenyl ester (880 mg, 94%) as a pale yellow waxy solid.

c) A solution of phosphoric acid dibenzyl ester 4-carboxyl-phenyl ester (205 mg, 0.5 mmol) (from step b) above) in $CH_2Cl_2$ (2 mL) was added to a solution of 1-ethyl-3-(3-dimethylaminopropyl)carbodiimide hydrochloride (149 mg, 0.78 mmol) (Aldrich) and Dimethylaminopyridine (139 mg, 1.13 mmol) in $CH_2Cl_2$ (5 mL). After 5 min., 1-Hydroxymethyl-3-(1-methyl-1H-indol-3-yl)-4-(1-methyl-6-nitro-1H-indol-3-yl)-pyrrole-2,5-dione (215 mg, 0.5 mmol), prepared as in example 1a, in $CH_2Cl_2$ (2 mL), was added and the mixture was stirred at room temperature for 3 h. The resulting mixture was partitioned between $CH_2Cl_2$ and water and the organic extracts were washed with water. The aqueous layer was extracted with $CH_2Cl_2$. The organic extracts were combined, dried ($MgSO_4$) and concentrated. Chromatography of the residue over silica gel using 5%–10% EtOAc-$CH_2Cl_2$ yielded 4-(bis-benzyloxy-phosphoryloxy)-benzoic acid 3-(1,6-dimethyl-1H-indol-3-yl)-4-(1-methyl-1H-indol-3-yl)-2,5-dioxo-2,5-dihydro-pyrrol-1-ylmethyl ester (179 mg, 44%) as an orange foam.

d) 1,4 Cyclohexadiene (0.12 mL, 1.26 mmol) (Aldrich) was added to a mixture of 4-(bis-benzyloxy-phosphoryloxy)-benzoic acid 3-(1,6-dimethyl-1H-indol-3-yl)-4-(1-methyl-1H-indol-3-yl)-2,5-dioxo-2,5-dihydro-pyrrol-1-ylmethyl ester (100 mg, 0.12 mmol) (from step c) above) and Pd/C (37 mg 10%) in a mixture of THF (6 mL) and ethanol (0.3 mL). The reaction mixture was warmed to 55° C. for 20 minutes. The reaction mixture was cooled to room temperature and was filtered over celite, washed with methylene chloride and concentrated. The residue was dissolved in MeCN and water at 0° C. 1N Sodium hydroxide (2.4 mL, 2.4 mmol) was added and the mixture was lyophilized. The resulting mixture was further purified by HPLC with 5 to 50% MeCN—water. Lyophilization yielded 4-phosphonoooxy-benzoic acid 3-(1-methyl-1H-indol-3-yl)-4-(1-methyl-6-nitro-1H-indol-3-yl)-2,5-dioxo-2,5-dihydro-pyrrol-1-ylmethyl ester monosodium salt (60 mg, 74%) as an orange powder.

Example 15

[[3-(1-Methyl-1H-indol-3-yl)-4-(1-methyl-6-nitro-1H-indol-3-yl)-2,5-dioxo-2,5-dihydro-pyrrol-1-yl]methoxycarbonyl]-4-phenyl-O-methylpolyethylene Glycol 500 a) Dry PEG-500 monomethyl ether (18.36 g, 33 mmol), ethyl-4-hydroxybenzoate (5.0 g, 30 mmol) and triphenylphosphine (17.34 g, 66 mmol) were dissolved in dry THF (100 mL) and cooled to 0° C. under argon. To this was slowly added diethylazodicarboxylate (12.95 mL, 83 mmol) in dry THF (10 mL). The resulting mixture was then warmed to 50° C. for 16 h. The mixture was cooled to 0° C. under argon and diethylazodicarboxylate (6 mL) in dry THF (5 mL) was added. The mixture was heated at 50° C. for 24 h. Evaporation of the solvents and chromatography of the residue over silica gel using 1:1 $CH_2Cl_2$-hexanes, $CH_2Cl_2$, 50% ether/—$CH_2Cl_2$, and ether yielded 9 g crude ethyl-4-O-methylpolyethylene glycol 500-benzoate as an oil, 5.4 g orange oil (3/2 mole % triphenylphosphine/product), and 4.9 g (~58% overall yield) orange oil (5/4 mole % triphenylphosphine/product).

b) To a solution of the crude ethyl-4-O-methylpolyethylene glycol 500-benzoate (4.90 g, 5/4 mole % triphenylphosphine/product) (from step a) above) in methanol (10 mL) and water (15 mL) was added 6N NaOH (1.3.8 mL, 83 mmol), and the resulting solution was heated to 65° C. for 2 h. The solution was concentrated and partitioned between 30% $CH_2Cl_2$/ethyl acetate and water. The aqueous layer was cooled to 0° C. and acidified to pH 3.0 with 1 N HCl. The mixture was extracted with $CH_2Cl_2$ and the organic extracts were dried ($MgSO_4$). Evaporation of the organic solvents gave crude 4-O-methylpolyethylene glycol 500-benzoic acid (2.3 g, 49%) as a yellow waxy residue. (sample contained 20–30% molar excess PEG 500).

c) A solution of the crude 4-O-methylpolyethylene glycol 500-benzoic acid (679 mg, 1 mmol) (from step b) above) in dry $CH_2Cl_2$ (5 mL) was added at room temperature to a solution of 1-ethyl-3-(3-dimethylaminopropyl) carbodiimide hydrochloride (300 mg, 1.56 mmol) (Aldrich) and dimethylaminopyridine (279 mg, 2.28 mmol) in dry $CH_2Cl_2$ (5 mL). After 5 min., 1-Hydroxymethyl-3-(1-methyl-1H-indol-3-yl)-4-(1-methyl-6-nitro-1H-indol-3-yl)-pyrrole-2,5-dione (430 mg, 1 mmol), prepared as in example 1a, was added. The mixture was stirred at room temperature for 4 h. Water was added and the mixture was extracted with $CH_2Cl_2$. The organic extracts were washed with water, dried over ($MgSO_4$) and concentrated. The residue was purified by HPLC with MeCN/water to give [[3-(1-methyl-1H-indol-3-yl)-4-(1-methyl-6-nitro-1H-indol-3-yl)-2,5-dioxo-2,5-dihydro-pyrrol-1-yl]methoxycarbonyl]-4-phenyl-O-methylpolyethylene glycol 500 (490 mg, 47%) as an orange oil.

Example 16

Carbonic Acid Allyl Ester 3-(1-Methyl-1H-indol-3-yl)-4-(1-methyl-6-nitro-1H-indol-3-yl)-2,5-dioxo-2,5-dihydro-pyrrol-1-ylmethyl Ester A solution of 200 mg (0.47 mmole) of 1-hydroxymethyl-3-(1-methyl-1H-indol-3-yl)-4-(1-methyl-6-nitro-1H-indol- 3-yl)-pyrrole-2,5-dione, prepared as in the example 1a, was dissolved in 90 ml of THF and treated with 300 mg (2.5 mmol) of 4-dimethylaminopyridine (DMAP). To this solution at 5° C. was added 90 mg (0.75 mmole) of allyl chloroformate. While still cool, 300 mg (2.4 mmol) of 1,5-diazabicyclo(4.3.0)non-5-ene (DBN) (Aldrich) was added dropwise. This was stirred for 14 hours at 20° C. The solvent was evaporated and the mixture was purified by chromatography using silica gel and eluting with a mixture of EtOAc/Hexane to afford carbonic acid allyl ester 3-(1-methyl-1H-indol-3-yl)-4-(1-methyl-6-nitro-1H-indol-3-yl)-2,5-dioxo-2,5-dihydro-pyrrol-1-ylmethyl ester as a red solid (m.p. 191–194° C.).

Example 17

(2-Dimethylamino-ethyl)-carbamic Acid 3-(1-Methyl-1H-indol-3-yl)-4-(1-methyl-6-nitro-1H-indol-3-yl)-2,5-dioxo-2,5-dihydro-pyrrol-1-ylmethyl Ester 1-Hydroxymethyl-3-(1-methyl-1H-indol-3-yl)-4-(1-methyl-6-nitro-1H-indol-3-yl)-pyrrole-2,5-dione (200 mg, 0.47 mmol), prepared as in example 1a, was dissolved in THF (10 mL). The resulting red solution was cooled in an ice bath. Lithium bis(trimethylsiliyl)amide (0.56 mL, 0.56 mmol, 1 M in THF) was added dropwise to the solution to give a red suspension. After 10 min, bis(p-nitrophenyl) carbonate (200 mg, 0.66 mmol) was added. The resulting solution was stirred at 0° C. for 20 min. Diethylaminoethylamine (90 mg, 0.78 mmol) in THF (2 mL) was added. Stirring was continued for 2 hrs. The mixture was evaporated and the residue was purified by flash chromatography to give (2-dimethylamino-ethyl)-carbamic acid 3-(1-methyl-1H-indol-3-yl)-4-(1-methyl-6-nitro-1H-indol-3-yl)-2,5-dioxo-2,5-dihydro-pyrrol-1-ylmethyl ester (124 mg 46%).

Example 18

[2-(2-Hydroxy-ethoxy)-ethyl]-carbamic Acid 3-(1-Methyl-1H-indol-3-yl)-4-(1-methyl-6-nitro-1H-indol-3-yl)-2,5-dioxo-2,5-dihydro-pyrrol-1-ylmethyl Ester This compound was prepared from 1-amino-2-ethoxy-ethanol (Aldrich), using the same procedure as in example 17 (45 mg, 17%).

Example 19

(2-Hydoxy-ethyl)-carbamic Acid 3-(1-Methyl-1H-indol-3-yl)-4-(1-methyl-6-nitro-1H-indol-3-yl)-2,5-dioxo-2,5-dihydro-pyrrol-1-ylmethyl Ester n-BuLi (0.96 mL, 1.54 mmol, 1.6 M in hexanes) was added drop-wise to a solution of 1-hydroxymethyl-3-(1-methyl-1H-indol-3-yl)-4-(1-methyl-6-nitro-1H-indol-3-yl)-pyrrole-2,5-dione (600 mg, 1.54 mmol), prepared as in example la, in THF (30 mL) at 0° C. After 10 min bis(p-nitrophenyl)carbonate (600 mg, 1.96 mmol) was added. The solution was stirred at 0° C. for 20 min. A solution of 1-aminoethanol (128 mg, 2.10 mmol) was added. The resulting mixture was stirred at 0° C. for 30 min. Aqueous $NH_4Cl$ was added and the mixture was extracted with EtOAc. The organic extract was washed with brine and dried over $MgSO_4$. Evaporation of the solvents and chromatography of the residue over silica gel using 1:1–3:2 EtOAc/hexanes gave (2-hydoxy-ethyl)-carbamic acid 3-(1-methyl-1H-indol-3-yl)-4-(1-methyl-6-nitro-1H-indol-3-yl)-2,5-dioxo-2, 5-dihydro-pyrrol-1-ylmethyl ester (339 mg, 47%).

Example 20

(2-Phosphonooxy-ethyl)-carbamic Acid 3-(1-Methyl-1H-indol-3-yl)-4-(1-methyl-6-nitro-1H-indol-3-yl)-2,5-dioxo-2,5-dihydro-pyrrol-1-ylmethyl Ester a) Triphenylphosphine (95 mg, 0.36 mmol) and dibenzyl phosphate (101 mg, 0.36 mmol) were added to a solution of (2-Hydoxy-ethyl)-carbamic acid 3-(1-methyl-1H-indol-3-yl)-4-(1-methyl-6-nitro-1H-indol-3-yl)-2,5-dioxo-2,5-dihydro-pyrrol-1-ylmethyl ester, prepared as in example 19 (150 mg, 0.289 mmol) in THF (6 mL). The mixture was cooled at −78° C. Diethyl azodicarboxiate (0.057 mL, 0.36 mmol) was added dropwise over 5 min. The cooling bath was removed and the mixture was stirred overnight. The mixture was then evaporated. Chromatography of the residue over silica gel using 2:1–4:1 EtOAc/hexanes gave [2-bis-benzyloxy-phosphoryloxy)-ethyl]-carbamic acid 3-(1-methyl-1H-indol-3-yl)-4-(1-methyl-6-nitro-1H-indol-3-yl)-2,5-dioxo-2,5-dihydro-pyrrol-1-ylmethyl ester (121 mg, 54%).

b) Pd/C (33 mg, 10%) and 1,4-cyclohexadiene (0.12 mL, 1.27 mmol) were added to a solution of [2-bis-benzyloxy-phosphoryloxy)-ethyl]-carbamic acid 3-(1-methyl-1H-indol-3-yl)-4-(1-methyl-6-nitro-1H-indol-3-yl)-2,5-dioxo-2,5-dihydro-pyrrol-1-ylmethyl ester (115 mg, 0.148 mmol) in a mixture of THF (5 mL) and EtOH (0.25 mL). The mixture was heated to 50–55° C. for 30 min. The resulting mixture was filtered through celite, washed with THF and the filtrate was evaporated. The residue was dissolved in a mixture of EtOH (10 mL) and $CH_3CN$ (10 mL). 0.1 N NaOH was added and the pH was adjusted to 8.2. Water (10 mL) was added to dissolve the precipitate. The organic solvents were removed under vacuum and lyophilisation of the red solution gave (2-phosphonooxy-ethyl)-carbamic acid 3-(1-methyl-1H-indol-3-yl)-4-(1-methyl-6-nitro-1H-indol-3-yl)-2,5-dioxo-2,5-dihydro-pyrrol-1-ylmethyl ester (59 mg, 62%) as an orange powder.

Example 21

3-(1-Methyl-1H-indol-3-yl)-4-(1-methyl-6-nitro-1H-indol-3-yl)-2,5-dioxo-2,5-dihydro-pyrrole-1-carboxylic Acid (2-Diethylamino-ethyl)-amide To a cold solution of 3-(1-Methyl-3-indolyl)-4-(1-methyl-6-nitro-3-indolyl)-1H-pyrrole-2,5-dione (200 mg, 0.5 mmol) (see Davis U.S. Pat. No. 5,057,614) in THF (7 mL) was added dropwise, lithium bis(trimethylsilyl)amide (0.55 mmol, 0.55 mL, 1 M in THF). The resulting red suspension was stirred for 15 min. Bis(p-nitrophenyl)carbonate (213 mg, 0.7 mmol) was added. The solution was stirred at 0° C. for 0.5 h. Diethylaminoethylamine (69.7 mg, 0.6 mmol) in THF (2 mL) was added, and stirring was continued for 2 h. The solvent was evaporated and the residue was purified by flash chromatography to give 3-(1-methyl-1H-indol-3-yl)-4-(1-methyl-6-nitro-1H-indol-3-yl)-2,5-dioxo-2,5-dihydro-pyrrole-1-carboxylic acid (2-diethylamino-ethyl)-amide (28 mg, 10%).

Example 22

3-(1-Methyl-1H-indol-3-yl)-4-(1-methyl-6-nitro-1H-indol-3-yl)-2,5-dioxo-2,5-dihydro-pyrrole-1-carboxylic Acid (6-Dimethylamino-hexyl)-amide This compound was prepared from dimethylaminohexylamine according to the procedure described in example 21 (67 mg, 24%).

Example 23

3-(1-Methyl-1H-indol-3-yl)-4-(1-methyl-6-nitro-1H-indol-3-yl)-2,5-dioxo-2,5-dihydro-pyrrole-1-carboxylic Acid (4-Hydroxybutyl)-amide

To a cold solution of 3-(1-methyl-3-indolyl)-4-(1-methyl-6-nitro-3-indolyl)-1H-pyrrole-2,5-dione (500 mg, 1.25 mmol) (see Davis U.S. Pat. No. 5,057,614) in THF (7 mL) was added dropwise n-butyllithium (0.86 mL, 1.375 mmol, 1.6 M in hexane). The resulting red suspension was stirred for 15 min. Bis(p-nitrophenyl)carbonate (532 mg, 1.75 mmol) was then added. The resulting solution was stirred at 0° C. for 1 h. 4-aminobutanol (167 mg, 1.875 mmol) in THF (4 mL) was added, and stirring was continued for 2 h. The solvent was evaporated and the residue was purified by flash chromatography to afford 3-(1-Methyl-1H-indol-3-yl)-4-(1-methyl-6-nitro-1H-indol-3-yl)-2,5-dioxo-2,5-dihydro-pyrrole-1-carboxylic acid (4-hydroxybutyl)-amide as an orange solid (280 mg, 43%).

Example 24

Phosphoric Acid Mono-(4-{[3-(1-methyl-1H-indol-3-yl)-4-(1-methyl-6-nitro-1H-indol-3-yl)-2,5-dioxo-2,5-dihydro-pyrrole-1-carbonyl]-amino}-butyl) Ester Sodium Salt a) Triphenylphosphine (0.86 g, 3.29 mmol) and Dibenzyl phosphate (0.91 g, 3.29 mmol) were added to a solution of 3-(1-methyl-1H-indol-3-yl)-4-(1-methyl-6-nitro-1H-indol-3-yl)-2,5-dioxo-2,5-dihydro-pyrrole-1-carboxylic acid (4-hydroxybutyl)-amide (prepared as in example 23, 1.41 g, 2.74 mmol) in THF (50 mL). The mixture was cooled to −78° C. Diethyl azodicarboxylate (0.52 mL, 3.29 mmol) was added dropwise over 5 min. The cooling bath was removed and after 2 h, the mixture was evaporated. Chromatography of the residue over silica gel using 2:1 EtOAc/hexane then EtOAc gave phosphoric acid dibenzyl ester 4-{[3-(1-methyl-1H-indol-3-yl)-4-(1-methyl-6-nitro-1H-indol-3-yl)-2,5-dioxo-2,5-dihydro-pyrrole-1-carbonyl]-amino}butyl ester (1.76 g, 83%).

b) Pd/C (0.5 g, 10%) and 1,4-cyclohexadiene (1.84 mL, 19 mmol) were added to a solution of phosphoric acid dibenzyl ester 4-{[3-(1-methyl-1H-indol-3-yl)-4-(1-methyl-6-nitro-1H-indol-3-yl)-2,5-dioxo-2,5-dihydro-pyrrole-1-carbonyl]-amino} butyl ester (1.76 g, 2.27 mmol) (from step a) above) in a mixture of THF (75 mL) and EtOH (3.8 mL). The resulting mixture was heated to 50–55° C. for 30 min. TLC (EtOAc) showed only a trace of phosphoric acid dibenzyl ester 4-{[3-(1-methyl-1H-indol-3-yl)-4-(1-methyl-6-nitro-1H-indol-3-yl)-2,5-dioxo-2,5-dihydro-pyrrole-1-carbonyl]-amino}-butyl ester left. The mixture was filtered through celite and the filtrate was evaporated. The residue was dissolved in a mixture of EtOH (100 mL) and $CH_3CN$ (100 mL) and basified with NaOH (0.2 N) to PH=8.2. Water (50 mL) was added to dissolve the precipitate. The organic solvents were removed under vacuum and lyophilisation of the red solution gave crude product (1.2 g). Purification of the residue using HPLC (10%–90% $CH_3CN$—$H_2O$) gave phosphoric acid mono-(4-{[3-(1-methyl-1H-indol-3-yl)-4-(1-methyl-6-nitro-1H-indol-3-yl)-2,5-dioxo-2,5-dihydro-pyrrole-1-carbonyl]-amino}-butyl) ester sodium salt (0.49 g, 34%) as a red powder.

Example 25

O-[2-[[[2,5-Dihydro-3-(1-Methyl-1H-indol-3-yl)-4-(1-Methyl-6-nitro-1H-indol-3-yl)-2,5-dioxo-1H-pyrrol-1-yl]methoxy]carbonyl]methyl]-O'-methylpolyethylene Glycol 2000

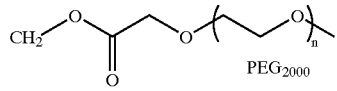

Poly(ethylene glycol)methyl ether average Mw ca. 2000 (Aldrich) (4.4 g, 2.2. mmol) in tetrahydrofuran (120 mL) was warmed to about 35–40° C. and to this was added sodium hydride (0.6 g of 60%, 15 mmol) and the mixture was stirred an additional 15 minutes. In two portions over 5 minutes, tert-butyl bromoacetate (1.2 g, ~6.2 mmol) was added and the mixture was heated at 45–50° C. for 4 hours. The mixture was cooled to about 30° C., diluted with ethyl ether (100 mL), filtered warm through celite and the filter cake washed with tetrahydrofuran. The organic solvents were removed by evaporation and the residue chromatographed on silica gel. Purified tert-butyl ester similarly prepared (12.5 g) was treated with trifluoroacetic acid (75 mL) and stirred at room temperature for 90 minutes. Evaporation of the solution and crystallization from cold ethyl ether gave 9.0 gram of methoxy PEG 2000 ethanoic acid.

A solution of methoxy PEG 2000 ethanoic acid (9.0 g, 4.5 mmol) in dichloromethane (50 mL) was treated with oxalyl chloride (10 mL), heated at gentle reflux for 15 minutes and followed by the addition of a trace of dimethylformamide (0.1 mL). Reflux was continued for an additional 15 minutes and toluene (50 mL) was added and the volatiles were removed by evaporation. The residue was dissolved in dichloromethane (50 mL) and added to a slurry of 1-hydroxymethyl-3-(1-methyl-1H-indol-3-yl)-4-(1-methyl-6-nitro-1H-indol-3-yl)-pyrrole-2,5-dione (1.93 g, 4.5 mmol) (prepared as in Example 1a) and 4-dimethylaminopyridine (1.1 g, 9 mmol) in dichloromethane (25 mL) at −50° C. The cooling bath was removed and the mixture was stirred at room temperature for 2 hours and poured onto silica gel (200 g) in dichloromethane. Purification by chromatography and crystallization of the residue from tetrahydrofuran-ethyl ether provided O-[2-[[2,5-dihydro-3-(1-methyl-1H-indol-3-yl)-4-(1-methyl-6-nitro-1H-indol-3-yl)-2,5-dioxo-2,5-dihydro-pyrrol-1-yl]methoxycarbonyl]methyl-O'-methylpolyethylene glycol 2000 as a red solid (yield 63%).

Example 26

Antiproliferative Activity

The antiproliferatiave activity of the compounds of the invention is demonstrated below. These effects indicate that the compounds of the present invention are useful in treating cancer, in particular solid tumors such as breast and colon tumors.

MDAMB-435 Cell-Based Assay

The epithelial breast carcinoma cell line (MDAMB-435) was purchased from ATCC (American Type Cell Culture Collection) and was grown in culture in medium as recommended by ATCC. For analysis of the effect of various compounds of formula I on the growth of these cells, the cells were plated at a concentration of 1500 cells/well in a 96 well tissue culture plate ("test plate"). The day after the cells were plated, the compounds to be analyzed were dissolved in 100% DMSO (dimethyl sulfoxide) to yield at 10 mM stock solution. Each compound was diluted in $H_2O$ to 1 mM and was added to triplicate wells in the first row of a 96 well master plate containing medium to yield a final concentration of 40 μM. The compounds were then serially diluted in medium in the "master plate". The diluted compound(s) were then transferred to test plates containing cells. A row of vehicle "control cells" received DMSO. The final concentration of DMSO in each well was 0.1%. 5 days post drug addition, the plate was analyzed as described below.

MTT (3-(4-5 methyl thiazole-2-yl)-2,5-diphenyl tetrazolium bromide; thiazolyl blue) was added to each well to yield a final concentration of 1 mg/ml. The plate was then incubated at 37° C. for 2½–3 hours. The MTT-containing medium was then removed and 50 μl of 100% ethanol was added to each well to dissolve the formazan. The absorbences were then read using an automated plate reader (Bio-tek microplate reader). $IC_{50}$'s were calculated using the Reed and Munsch-equation, see Am. J. Hygiene Vol. 27 pgs. 493–497, 1938.

The results of the foregoing in vitro experiments are set forth in Table I below.

Each of the compounds in Table I had an $IC_{50} \leq 1.00$ μM.

TABLE I

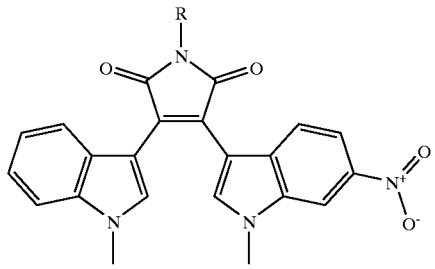

| Example | R | Scheme |
|---|---|---|
| 6b | ![structure] CH₂-O-C(=O)-C(CH₃)₃ | Ia |
| 7 | ![structure] CH₂-O-C(=O)-cyclohexyl-NH₂ | Ia |
| 8b, 11 | ![structure] CH₂-O-C(=O)-C(CH₃)₂-NH₂ | Ia |
| 8a, 9, 10 | ![structure] CH₂-O-C(=O)-piperidinyl-NH | Ia |
| 13 | ![structure] CH₂-O-C(=O)-piperidinyl-N-C(=O)-CH₂CH₂-O-(CH₂CH₂O)ₙ- PEG₁₀₀₀ | Ib |

TABLE I-continued
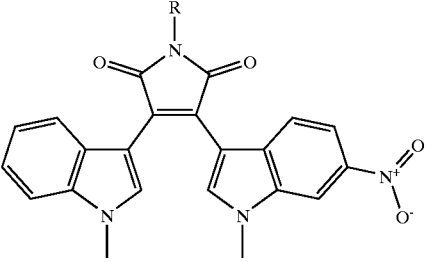
| Example | R | Scheme |
|---------|---|--------|
| 12 | 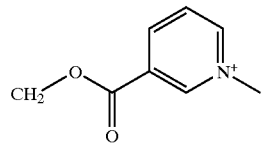 | Ib |
| 2 | 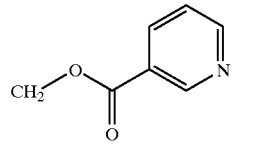 | Ib |
| 3a | 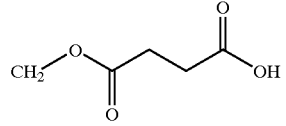 | Ib |
| 3f | 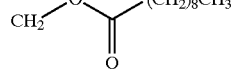 | Ib |
| 5 | 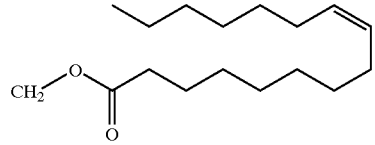 | Ia |
| 3g | 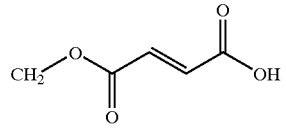 | Ib |
| 4 | 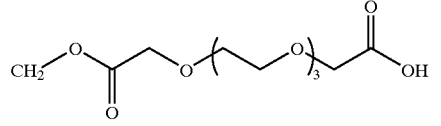 | Ib |
| 3h | 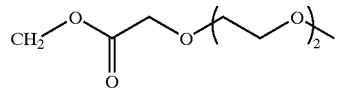 | Ib |
| 6a |  | Ia |

TABLE I-continued
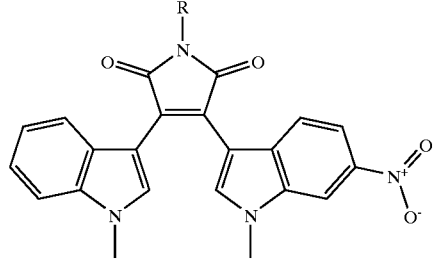
| Example | R | Scheme |
|---|---|---|
| 3b | 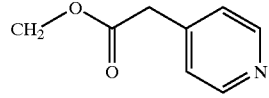 PEG$_{2000}$ | Ib |
| 3c | 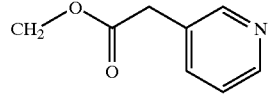 | Ib |
| 3d | 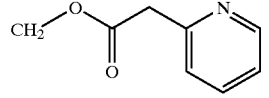 | Ib |
| 3e | 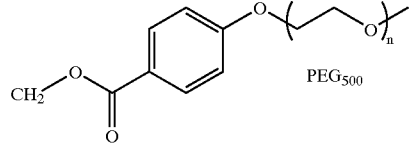 | Ib |
| 15 | 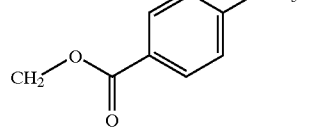 PEG$_{500}$ | Ib |
| 14 | 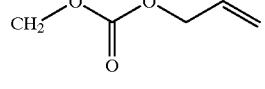 | Ib |
| 16 | 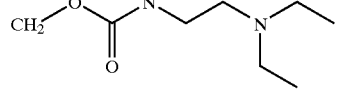 | III |
| 17 | 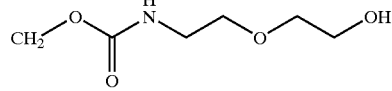 | IV |
| 18 | 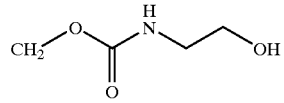 | IV |
| 19 | | IV |

TABLE I-continued

[Structure: bisindolylmaleimide with N-R substituent, one indole N-methyl, other indole N-methyl with 6-nitro group]

| Example | R | Scheme |
|---------|---|--------|
| 20 | CH₂-O-C(=O)-NH-CH₂CH₂-OPO₃Na₂ | IV |
| 1 | CH₂OPO₃Na₂ | II |
| 21 | CHO-NH-CH₂CH₂-N(Et)₂ | V |
| 22 | CHO-NH-(CH₂)₄-N(CH₃)₂ | V |
| 23 | CHO-NH-(CH₂)₄-OH | V |
| 24 | CHO-NH-(CH₂)₄-OPO₃Na₂ | V |
| 25 | CH₂-O-C(=O)-CH₂-O-(CH₂CH₂O)ₙ- PEG₂₀₀₀ | Ib |
|  | CHO-NH-CH₂CH₂-O-(CH₂CH₂O)ₙ- PEG₂₀₀₀ | V |
|  | CHO-NH-CH₂-C(=O)-O-CH₂CH₃ | V |
|  | CHO-NH-CH₂CH₂-O-CH₂CH₂-OH | V |
|  | CHO-NH-CH₂CH₂-C₆H₅ | V |

TABLE I-continued

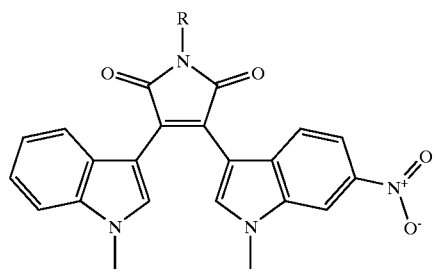

| Example | R | | Scheme |
|---|---|---|---|
| | | | IV |
| 1 | —CH₂OH | | I |

Plasma conversion measurements of representative compounds of formula I indicate that these compounds in fact yield pharmaceutically active metabolites within time frames appropriate for therapeutic use. Moreover, stability measurements also for certain representative compounds of formula I show in addition that these compounds have fair to good stability in the types of solutions typically used to administer therapeutic drugs intravenously. The results of these plasma conversion and stability measurements are set forth in Table II below. Thus, these compounds are suitable for administration to patients by continuous infusion.

TABLE II

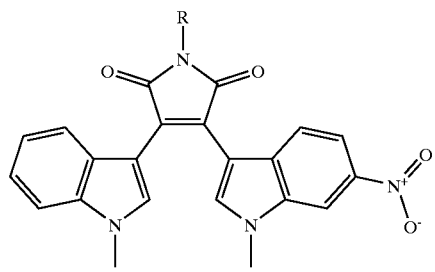

| Example | R | Stability | Plasma Conversion | Scheme |
|---|---|---|---|---|
| 8a, 9, 10 | | Good | 30% @ 30 min | Ia |
| 13 | | Good | N/D* | Ib |

TABLE II-continued

| Example | R | Stability | Plasma Conversion | Scheme |
|---|---|---|---|---|
| 12 | CH₂-O-C(O)-(3-pyridinium-N-methyl) | Fair | 60% @ 30 min | Ib |
| 3a | CH₂-O-C(O)-(3-pyridyl) | Good | 70% @ 30 min | Ib |
| 3f | CH₂-O-C(O)-CH₂CH₂-COOH | Good | 20% @ 30 min | Ib |
| 3g | CH₂-O-C(O)-(CH₂)₇-CH=CH-(CH₂)₅-CH₃ (oleate) | Good | N/D* | Ib |
| 3h | CH₂-O-C(O)-CH₂-O-(CH₂CH₂O)₃-CH₂-COOH | Fair | N/D* | Ib |
| 3b | CH₂-O-C(O)-CH₂CH₂-O-(CH₂CH₂O)ₙ— PEG₂₀₀₀ | Good | 80% @ 30 min | Ib |
| 3c | CH₂-O-C(O)-CH₂-(4-pyridyl) | Good | 60% @ 30 min | Ib |
| 3d | CH₂-O-C(O)-CH₂-(3-pyridyl) | Good | 70% @ 30 min | Ib |
| 15 | CH₂-O-C(O)-(4-(O-(CH₂CH₂O)ₙ—)-phenyl) PEG₅₀₀ | Good | 100% @ 2 hrs | Ib |

TABLE II-continued
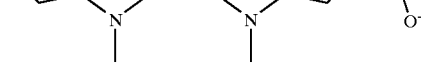
| Example | R | Stability | Plasma Conversion | Scheme |
|---|---|---|---|---|
| 14 | 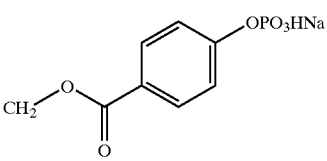 | Good | 5% @ 4 hrs | Ib |
| 17 | 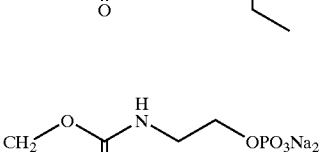 | Good | 15% @ 6 hrs | IV |
| 20 | 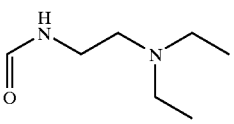 | Good | N/D* | IV |
| 1 | CH$_2$OPO$_3$Na$_2$ | Good | 100% @ 30 min | II |
| 21 | 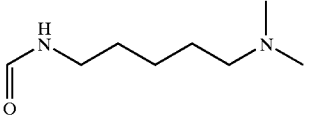 | Fair | 100% @ 1 hr | V |
| 22 | 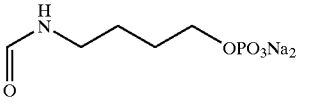 | Good | N/D* | V |
| 24 | 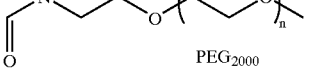 | Good | 10% @ 6 hrs | V |
|  | PEG$_{2000}$ | Good | N/D* | V |

EXAMPLE 27

Tablet Formulation

| Item | Ingredients | | | Mg/Tablet | | | |
|---|---|---|---|---|---|---|---|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound of the invention.

Manufacturing Procedure:

1. Mix items 1, 2 and 3 in a suitable mixer for 15 minutes.
2. Granulate the powder mix from step 1 with 20% Povidone K30 Solution (Item 4).
3. Dry the granulation from step 2 at 50° C.
4. Pass the granulation from step 3 through a suitable milling equipment.
5. Add the item 5 to the milled granulation step 4 and mix for 3 minutes.
6. Compress the granulation from step 5 on a suitable press.

Example 28: Capsule Formulation

| Item | Ingredients | | | mg/capsule | | |
|---|---|---|---|---|---|---|
| 1 | Compound A* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound A represents a compound of the invention.

Manufacturing Procedure:

1. Mix items 1, 2 and 3 in a suitable mixer for 15 minutes.
2. Add items 4 & 5 and mix for 3 minutes.
3. Fill into a suitable capsule.

Example 29: Injection Solution/Emulsion Preparation

| Item | Ingredient | mg/mL |
|---|---|---|
| 1 | Compound A* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound A represents a compound of the invention.

Manufacturing Procedure:

1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

Example 30: Injection Solution/Emulsion Preparation

| Item | Ingredient | mg/mL |
|---|---|---|
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound A represents a compound of the invention.

Manufacturing Procedure:

1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:

1. A compound having the formula

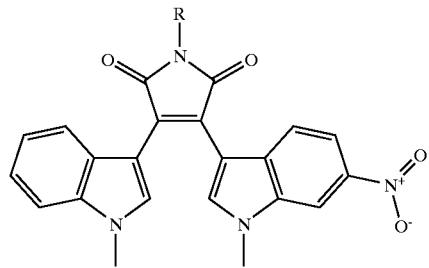

I and pharmaceutically active salts of said compounds, wherein:

R is selected from the group consisting of $-CH_2OPO_3R^1R^2$, $-CH_2OH-CH_2OCOR^3$, $-H_2OCO_2R^3$, $-CH_2OCONHR^3$, and $-CONHR^3$;

$R^1$ and $R^2$ are selected from the group consisting of H, Na and $NH_4$ and are the same unless either $R^1$ or $R^2$ is H, in which case the other can be different, or alternatively, $R^1$ and $R^2$ together represent calcium;

$R^3$ is selected from the group consisting of
alkyl which optionally may be substituted by one or more substituents selected from the group consisting of $-CO_2R^4$, $-NR^5R^6$, polyethylene glycol, $-OPO_3R^1R^2$, hydroxy, alkoxy and aryl; alkenyl which optionally may be substituted by one or more substituents selected from the group consisting of $-CO_2R^4$, $-NR^5R^6$, polyethylene glycol, $-OPO_3R^1R^2$, hydroxy, alkoxy and aryl; cycloalkyl which optionally may be substituted by one or more substituents selected from the group consisting of $-CO_2R^4$, $-NR^5R^6$, polyethylene glycol, $-OPO_3R^1R^2$, hydroxy, alkoxy and aryl,
heterocycle, which when having N as a heteroatom, the N optionally may be substituted with the group consisting of lower alkyl and $-COR^7$, and aryl which optionally may be substituted by one or more substituents selected from the group consisting of $CO_2R^4$, hydroxy, alkoxy, polyethylene glycol, $OPO_3R^1R^2$, and alkyl which itself may be substituted with hydroxy alkoxy, carboxy and substituted amino, provided that when aryl represents pyridine, the nitrogen may be substituted with lower alkyl;

$R^4$ is selected from the group consisting of H, Na and lower alkyl;

$R^5$ and $R^6$ are each independently selected from the group consisting of H, lower alkyl, and $-COR^7$, or alternatively, the group $-NR^5R^6$ together form a 5 or 6 membered heterocyclic ring; and $R^7$ is lower alkyl which optionally may be substituted with carboxy, polyethylene glycol, and substituted amino.

2. A compound having the formula

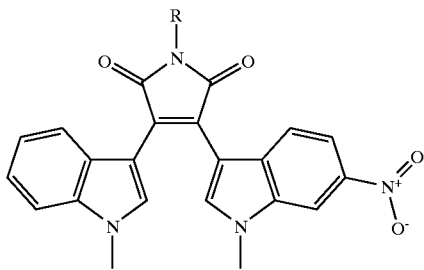

I and pharmaceutically active salts of said compounds, wherein:

R is selected from the group consisting of $-CH_2OPO_3R^1R^2$, $-CH_2OCOR^3$, $-CH_2OCO_2R^3$, $-CH_2OCONHR^3$, and $-CONHR^3$;

$R^1$ and $R^2$ are selected from the group consisting of H, Na and $NH_4$ and are the same unless either $R^1$ or $R^2$ is H, in which case the other can be different, or alternatively, $R^1$ and $R^2$ together represent calcium;

$R^3$ is selected from the group consisting of
  alkyl which optionally may be substituted by one or more substituents selected from the group consisting of $-CO_2R^4$, $-NR^5R^6$, polyethylene glycol, $-OPO_3R^1R^2$, hydroxy, alkoxy and aryl; alkenyl which optionally may be substituted by one or more substituents selected from the group consisting of $-CO_2R^4$, $-NR^5R^6$, polyethylene glycol, $-OPO_3R^1R^2$, hydroxy, alkoxy and aryl; cycloalkyl which optionally may be substituted by one or more substituents selected from the group consisting of $-CO_2R^4$, $-NR^5R^6$, polyethylene glycol, $-OPO_3R^1R^2$, hydroxy, alkoxy and aryl,
  heterocycle, which when having N as a heteroatom, the N optionally may be substituted with the group consisting of lower alkyl and $-COR^7$, and
  aryl which optionally may be substituted by one or more substituents selected from the group consisting of $CO_2R^4$, hydroxy, alkoxy, polyethylene glycol, $OPO_3R^1R^2$, and alkyl which itself may be substituted with hydroxy alkoxy, carboxy and substituted amino, provided that when aryl represents pyridine, the nitrogen may be substituted with lower alkyl;

$R^4$ is selected from the group consisting of H, Na and lower alkyl;

$R^5$ and $R^6$ are each independently selected from the group consisting of H, lower alkyl, and $-COR^7$, or alternatively, the group $-NR^5R^6$ together form a 5 or 6 membered heterocyclic ring; and $R^7$ is lower alkyl which optionally may be substituted with carboxy, polyethylene glycol, and substituted amino.

3. The compound of claim 2 wherein R is selected from the group consisting of $-CH_2OPO_3R^1R^2$ and $-CH_2OCOR^3$.

4. The compound of claim 2 wherein R is $-CH_2OCO$-pyridine, wherein the N atom on the pyridine is substituted with lower alkyl.

5. The compound of claim 4 wherein the N atom on the pyridine is substituted with methyl or ethyl.

6. The compound of claim 2 wherein $R^1$ and $R^2$ are independently selected from the group consisting of H and Na.

7. The compound of claim 2 wherein $R^3$ is heterocycle containing at least one nitrogen atom that optionally may be substituted with $-COR^7$.

8. The compound of claim 2 wherein $R^3$ is aryl which is substituted with $-OPO_3R^1R^2$, and $R^1$ and $R^2$ are independently selected from H and Na.

9. The compound of claim 2 wherein $R^3$ is aryl which is substituted by the group consisting of $-CO_2Na$, polyethylene glycol and $-CH_2CH_2N(CH_2CH_2)_2$.

10. The compound of claim 2 wherein $R^3$ is lower alkyl which is substituted with $-CO_2Na$.

11. The compound of claim 2 wherein the group $NR^5R^6$ together forms a 5 or 6 membered heterocyclic ring.

12. The compound of claim 11 wherein the group $NR^5R^6$ is selected from piperidine or pyrrolidine.

13. The compound of claim 2 wherein $R^5$ and $R^6$ are each independently selected from the group consisting of H, methyl and ethyl.

14. The compound of claim 2 wherein $R^7$ is ethyl which is substituted with polyethylene glycol.

15. The compound of claim 2 wherein R is $-CH_2OCOR^3$ and $R^3$ is ethyl which is substituted with polyethylene glycol having a molecular weight of about 750 to about 5000 Daltons.

16. The compound of claim 2 wherein the polyethylene glycol has a molecular weight of about 750 to about 5000 Daltons.

17. A compound selected from the group consisting of:
Phosphoric acid mono-[3-(1-methyl-1H-indol-3-yl)-4-(1-methyl-6-nitro-1H-indol-3-yl)-2,5-dioxo-2,5-dihydro-pyrrol-1-ylmethyl]sodium salt,
1-hydroxymethyl-3-(1-methyl-1H-indol-3-yl)-4-(1-methyl-6-nitro-1H-indol-3-yl)-pyrrole-2,5-dione,
Isonicotinic acid 3-(1-methyl-1H-indol-3-yl)-4-(1-methyl-6-nitro-1H-indol-3-yl)-2,5-dioxo-2,5-dihydro-pyrrol-1-ylmethyl ester,
But-2-enedioic acid mono-[3-(1-methyl-1H-indol-3-yl)-4-(1-methyl-6-nitro-1H-indol-3-yl)-2,5-dioxo-2,5-dihydro-pyrrol-1-ylmethyl]ester,
Decanoic acid 3-(1-methyl-1H-indol-3-yl)-4-(1-methyl-6-nitro-1H-indol-3-yl)-2,5-dioxo-2,5-dihydro-pyrrol-1-ylmethyl ester,
3-amino-cyclohexanecarboxylic acid 3-(1-methyl-1H-indol-3-yl)-4-(1-methyl-6-nitro-1H-indol-3-yl)-2,5-dioxo-2,5-dihydro-pyrrol-1-ylmethyl ester trifluoroacetate,
Piperidine-4-carboxylic acid 3-(1-methyl-1H-indol-3-yl)-4-(1-methyl-6-nitro-1H-indol-3-yl)-2,5-dioxo-2,5-dihydro-pyrrol-1-ylmethyl ester acetate salt,
Piperidine-4-carboxylic acid 3-(1-methyl-1H-indol-3-yl)-4-(1-methyl-6-nitro-1H-indol-3-yl)-2,5-dioxo-2,5-dihydro-pyrrol-1-ylmethyl ester hydrochloride, 2-amino-2-methyl-propionic acid 3-(1-methyl-1H-indol-3-yl)-4-(1-methyl-6-nitro-1H-indol-3-yl)-2,5-dioxo-2,5-dihydro-pyrrol-1-ylmethyl ester hydrochloride, 1-Methyl-3-[3-(1-methyl-1H-indol-3-yl)-4-(1-methyl-6-nitro-1H-indol-3-yl)-2,5-dioxo-2,5-dihydro-pyrrol-1-ylmethoxycarbonyl]-pyridinium; trifluoroacetate, and O-[2-[[4-[[[2,5-Dihydro-3-(1-methyl-1H-indol-3-yl)-4-(1-methyl-6-nitro-1H-indol-3-yl)-2,5-dioxo-1H-pyrrol-1-yl]methoxy]carbonyl]-1-piperidinyl]carbonyl]ethyl]-O'-methylpolyethylene glycol 1000.

18. A compound selected from the group consisting of:

4-Phosphonooxy-benzoic acid 3-(1-methyl-1H-indol-3-yl)-4-(1-methyl-6-nitro-1H-indol-3-yl)-2,5-dioxo-2,5-dihydro-pyrrol-1-ylmethyl ester monosodium salt,

[[3-(1-methyl-1H-indol-3-yl)-4-(1-methyl-6-nitro-1H-indol-3-yl)-2,5-dioxo-2,5-dihydro-pyrrol-1-yl]methoxycarbonyl]-4-phenyl-O-methylpolyethylene glycol 500, Carbonic acid allyl ester 3-(1-methyl-1H-indol-3-yl)-4-(1-methyl-6-nitro-1H-indol-3-yl)-2,5-dioxo-2,5-dihydro-pyrrol-1-ylmethyl ester, (2-Dimethylamino-ethyl)-carbamic acid 3-(1-methyl-1H-indol-3-yl)-4-(1-methyl-6-nitro-1H-indol-3-yl)-2,5-dioxo-2,5-dihydro-pyrrol-1-ylmethyl ester,

[2-(2-Hydroxy-ethoxy)-ethyl]-carbamic acid 3-(1-methyl-1H-indol-3-yl)-4-(1-methyl-6-nitro-1H-indol-3-yl)-2,5-dioxo-2,5-dihydro-pyrrol-1-ylmethyl ester, (2-Hydoxy-ethyl)-carbamic acid 3-(1-methyl-1H-indol-3-yl)-4-(1-methyl-6-nitro-1H-indol-3-yl)-2,5-dioxo-2,5-dihydro-pyrrol-1-ylmethyl ester, (2-phosphonooxy-ethyl)-carbamic acid 3-(1-methyl-1H-indol-3-yl)-4-(1-methyl-6-nitro-1H-indol-3-yl)-2,5-dioxo-2,5-dihydro-pyrrol-1-ylmethyl ester, 3-(1-Methyl-1H-indol-3-yl)-4-(1-methyl-6-nitro-1H-indol-3-yl)-2,5-dioxo-2,5-dihydro-pyrrole-1-carboxylic acid (2-diethylamino-ethyl)-amide, 3-(1-Methyl-1H-indol-3-yl)-4-(1-methyl-6-nitro-1H-indol-3-yl)-2,5-dioxo-2,5-dihydro-pyrrole-1-carboxylic acid (6-dimethylamino-hexyl)-amide, 3-(1-Methyl-1H-indol-3-yl)-4-(1-methyl-6-nitro-1H-indol-3-yl)-2,5-dioxo-2,5-dihydro-pyrrole-1-carboxylic acid (4-hydroxybutyl)-amide, and Phosphoric acid mono-(4-{[3-(1-methyl-1H-indol-3-yl)-4-(1-methyl-6-nitro-1H-indol-3-yl)-2,5-dioxo-2,5-dihydro-pyrrole-1-carbonyl]-amino}butyl)ester sodium salt.

19. A compound selected from the group consisting of:

phosphoric acid mono-[3-(1-methyl-1H-indol-3-yl)-4-(1-methyl-6-nitro-1H-indol-3-yl)-2,5-dioxo-2,5-dihydro-pyrrol-1-ylmethyl]sodium salt, O-[2-[[2,5-dihydro-3-(1-methyl-1H-indol-3-yl)-4-(1-methyl-6-nitro-1H-indol-3-yl)-2,5-dioxo-2,5-dihydro-pyrrol-1-yl]methoxycarbonyl]ethyl]-O'-methylpolyethylene glycol 2000, phosphoric acid mono-(4-{[3-(1-methyl-1H-indol-3-yl)-4-(1-methyl-6-nitro-1H-indol-yl)-2,5-dioxo-2,5-dihydropyrrole-1-carbonyl]-amino}butyl)ester sodium salt, 1-methyl-3-[3-(1-methyl-1H-indol-3yl)-4-(1-methyl-6-nitro-1H-indol-3-yl)-2,5-dioxo-2,5-dihydro-pyrrol-1-ylmethoxycarbonyl]-pyridinium trifluoroacetate, and O-[2-[[[2,5-Dihydro-3-(1-methyl-1H-indol-3-yl)-4-(1-methyl-6-nitro-1H-indol-3-yl)-2,5-dioxo-1H-pyrrol-1-yl]methoxy]carbonyl]methyl]-O'-methylpolyethylene glycol 2000.

20. A pharmaceutical composition comprising as an active ingredient an effective amount of a compound of claim 1 and a pharmaceutically acceptable carrier or excipient.

21. The pharmaceutical composition of claim 20 which is suitbale for parenteral administration.

22. A method for treating cancer comprising administering to a patient in need thereof a therapeutically effective amount of a compound according to claim 1.

23. The method of claim 22 wherein the cancer is a solid tumor.

24. The method of claim 22 wherein the cancer is breast, colon, or lung cancer.

\* \* \* \* \*

UNITED STATES PATENT AND TRADEMARK OFFICE
CERTIFICATE OF CORRECTION

PATENT NO. : 6,559,164 B1
DATED : May 6, 2003
INVENTOR(S) : Nader Fotouhi et al.

It is certified that error appears in the above-identified patent and that said Letters Patent is hereby corrected as shown below:

<u>Column 38,</u>
Line 47, "-$H_2OCO_2R^3$," should read -- -$CH_2OCO_2R^3$, --.

<u>Column 41,</u>
Line 29, "(2-Hydoxy-ethyl)" should read -- (2-Hydroxy-ethyl) --.

<u>Column 42,</u>
Line 19, "dihydropyrrole" should read -- dihydro-pyrrole --.
Line 21, "(1-methyl-1H-indol-3yl)" should read -- (1-methyl-1H-indol-3-yl) --.
Line 33, "suitbale" should read -- suitable --.

Signed and Sealed this

Sixteenth Day of September, 2003

JAMES E. ROGAN
*Director of the United States Patent and Trademark Office*